US007261896B2

(12) United States Patent
Hallenbeck et al.

(10) Patent No.: US 7,261,896 B2
(45) Date of Patent: Aug. 28, 2007

(54) METHODS FOR PREVENTING STROKES BY INDUCING TOLERANCE TO E-SELECTIN

(75) Inventors: John M. Hallenbeck, Kensington, MD (US); Hidetaka Takeda, Rockville, MD (US); Maria Spatz, Bethesda, MD (US)

(73) Assignee: United States of America as represented by the Secretary of the Department of Health and Human Services National Institutes of Health, Washington, DC (US)

( * ) Notice: Subject to any disclaimer, the term of this patent is extended or adjusted under 35 U.S.C. 154(b) by 0 days.

(21) Appl. No.: 10/296,423

(22) PCT Filed: May 23, 2001

(86) PCT No.: PCT/US01/16583

§ 371 (c)(1),
(2), (4) Date: Jun. 11, 2003

(87) PCT Pub. No.: WO01/89557

PCT Pub. Date: Nov. 29, 2001

(65) Prior Publication Data

US 2004/0009125 A1    Jan. 15, 2004

Related U.S. Application Data

(60) Provisional application No. 60/206,693, filed on May 24, 2000.

(51) Int. Cl.
*A61K 39/00* (2006.01)
*A61K 38/00* (2006.01)

(52) U.S. Cl. .......................... 424/185.1; 514/8
(58) Field of Classification Search ............. 424/185.1; 514/8; 530/350
See application file for complete search history.

(56) References Cited

FOREIGN PATENT DOCUMENTS

WO    WO-93 16724 A    9/1993

OTHER PUBLICATIONS

Federal Occupational Health. New vaccine may proivde hope to people at rish for stroke. Mar. 24, 2005.*
Feuerstein et al. Immune tolerance and Stroke: A turning Point. Stroke. Sep. 2002;33(9):2163-4.*
Takeda et al. In spontaneously hypertensive, genetically stroke-porne rate (SHR-SP), induction of mucosal tolerance to E-selectin prevents ischemic and hemorrhagic stroke. Stroke Symposium 2002. 114.*
Huang et al. Postischemic cerebrovascular E-selectin expression mediates tissue injury in murine stroke. Stroke. Dec. 2000;31(12):3047-53.*
Abel, B., Common Condition Emerges as possible stroke cause. HealthLink Medical College of Wisconsin. Apr. 4, 2005, 1-3.*
Simundic et al. Soluble adhesion molecules in acute ischemic stroke. Clin Invest Med. Apr. 2004;27(2):86-92.*
Barsoum et al. Effect of microencapsulated ampicillin on cell-mediated immune responses in mice. J Antimicrob Chemother. Nov. 1997;40(5):721-4.*
Szalai et al. The Arthus Reaction in Rodents: Species-Specific Requirement of Complement. The Journal of Immunology, 2000, 164: 463-468.*
Endler et al. The E-selectin S128R polymorphism is not a risk factor for coronary artery disease in patients with diabetes mellitus type 2. Thromb Res. 2003;112(1-2):47-50.*
G. del Zoppo et al.: "Inflammation and Stroke: Putative Role for Cytokines, Adhesion Molecules and iNOS in Brain Response to Ischemia." Brain Pathology, vol. 10, No. 1, Jan. 2000, pp. 95-112, XP002197635.
X. Wang et al.: "Demonstration of Increased Endothelial-Leukocyte Adhesion Molecule-1 mRNA Expression in Rat Ischemic Cortex." STROKE, vol. 26, No. 9, Sep. 1995, pp. 1665-1669, XP001064744.
Chen, Yong, et al., "Mucosal tolerance to E-selectin provides cell-mediated protection against ischemic brain injury", *PNAS*, Nol. 100, No. 225, (Dec. 9, 2003), 15107-15112.
Erkinjuntti, Timo, "Vascular Cognitive Impairment and Dementia", *Stroke: Pathophysiology, Diagnosis, and Management*, Chapter 29, 648-660.
Sacco, Ralph L., et al., "Classification of Ischemic Stroke", *Stroke: Pathophysiology, Diagnosis, and Management*, Chapter 4, 61-74.
Sughrue, M. E., et al., "Anti-adhesion molecule strategies as potential neuroprotective agents in cerebral ischemia: a critical review of the literature", *Inflammation Research*, 53(10), (Oct. 2004), 497-508.
Takeda, Hidetaka, et al., "Induction of Mucosal Tolerance to E-Selection Prevents Ischemic and Hemorrhagic Stroke in Spontaneously Hypertensive Genetically Stroke-Prone Rats", *Stroke, vol. 33, Expedited Publication*, (2002), 2156-2164.

* cited by examiner

*Primary Examiner*—Maher M. Haddad
(74) *Attorney, Agent, or Firm*—Schwegman, Lundberg, Woessner and Kluth P.A.

(57) ABSTRACT

The present invention provides a method for reducing stroke-related tissue damage by treating a mammal with E-selectin. Preferably, this treatment induces E-selectin tolerance in the mammal. Another aspect of the invention is a method for inducing E-selectin tolerance in a mammal through intranasal administration of E-selectin, preferably including booster administrations. The present methods are especially adapted for use in patients at increased risk of stroke or who may become at increased risk of stroke.

6 Claims, 7 Drawing Sheets

METHODS FOR PREVENTING STROKES BY INDUCING TOLERANCE TO E-SELECTIN

CROSS-REFERENCE TO RELATED APPLICATIONS

This application is a national stage application under 35 U.S.C. 371 of PCT/US01/16583, filed May 23, 2001, which claimed priority under 35 U.S.C. 119 of U.S. Provisional Patent Application No.: 60/206,693, filed May 24, 2000.

FIELD OF THE INVENTION

The present invention relates to methods for treating or preventing strokes and methods for inducing tolerance to E-selectin. The present methods are especially adapted for use in patients at increased risk of stroke or who may become at increase risk of stroke.

BACKGROUND

E-selectin (also known as ELAM-1, CD62, and CD62E) is a cytokine inducible cell surface glycoprotein cell adhesion molecule that is found exclusively on endothelial cells. E-selectin mediates the adhesion of various leukocytes, including neutrophils, monocytes, eosinophils, natural killer (NK) cells, and a subset of T cells, to activated endothelium (Bevilacqua, et al., "Endothelial leukocyte adhesion molecule 1: an inducible receptor for neutrophils related to complement regulatory proteins and lectins," *Science* 243; 1160 (1989); Graber, et al., "T cells bind to cytokine-activated endothelial cells via a novel, inducible sialoglycoprotein and endothelial leukocyte adhesion molecule-1" *J. Immunol.* 145: 819 (1990); Carlos, et al., "Human monocytes bind to two cytokine-induced adhesive ligands on cultured human endothelial cells: endothelial-leukocyte adhesion molecule-1 and vascular cell adhesion molecule-1" *Blood* 77: 2266 (1991); Hakkert, et al., "Neutrophil and monocyte adherence to and migration across monolayers of cytokine-activated endothelial cells: the contribution of CD18, ELAM-1, and VLA-4" *Blood* 78: 2721 (1991); and Picker, et al., "ELAM-1 is an adhesion molecule for skin-homing T cells" *Nature* 349: 796 (1991)).

The expression of E-selectin is induced on human endothelium in response to the cytokines IL-1 and TNF, as well as bacterial lipopolysaccharide (LPS), through transcriptional upregulation (Montgomery, et al., "Activation of endothelial-leukocyte adhesion molecule 1 (ELAM-1) gene transcription" *Proc. Natl. Acad. Sci.* 88: 6523 (1991)). E-selectin is expressed in vascular endothelial tissue where cells have been activated. Pober, J. S., et al., "Two distinct monokines, interleukin 1 and tumor necrosis factor, each independently induce biosynthesis and transient expression of the same antigen on the surface of cultured human vascular endothelial cells," *J. Immunol.* 136: 1680 (1986); Bevilacqua M. P., et al., "Identification of an inducible endothelial-leukocyte adhesion molecule," Proc. Natl. Acad. Sci. 84: 9238 (1987). Activation of vascular endothelial cells is believed, in at least some cases, to be involved in inflammatory vascular tissue damage leading to thrombosis (Fareed, J. et al., "Molecular markers of hemostatic activation. Implications in the diagnosis of thrombosis, vascular, and cardiovascular disorders," *Clin. Lab. Med.* 15: 39 (1995)).

It is well-established that vascular tissue damage and thrombosis are involved in the development of strokes. Decreased supply of oxygen and nutrients from the blood to brain cells due to vascular tissue damage and thrombosis leads to the death of brain cells, the clinical manifestations of a stroke, and causes the formation of detectable spaces left by these cells, called infarctions. Strokes are a major cause of mortality in the world and account for tens of billions of dollars of medical costs in the United States alone. Although some treatments for stroke prevention are available, there is a need for more effective treatments that are applicable to a larger fraction of afflicted patients.

Structurally, E-selectin belongs to a family of adhesion molecules termed "selectins" that also includes P-selectin and L-selectin (see reviews in Lasky, "Selectins: interpreters of cell-specific carbohydrate information during inflammation" *Science* 258: 964 (1992) and Bevilacqua and Nelson, "Selectins" *J. Clin. Invest.* 91: 379 (1993)). These molecules are characterized by common structural features such as an amino-terminal lectin-like domain, an epidermal growth factor (EGF) domain, and a discrete number of complement repeat modules (approximately 60 amino acids each) similar to those found in certain complement binding proteins.

Recently, new methods and pharmaceutical formulations have been found that induce tolerance, orally or mucosally (e.g., by intranasal administration, using as tolerizers autoantigens, bystander antigens, or disease-suppressive fragments or analogs of autoantigens or bystander antigens). Such treatments are described in Wiener, H. et al., "Bystander suppression of autoimmune diseases," WO9316724 (1993); Brigham & Womens Hospital (US), "Enhancement of the down-regulation of autoimmune diseases by oral administration of autoantigens," WO9112816 (1991); Weiner, H. et al., "Improved treatment of autoimmune diseases by aerosol administration of auto antigens," WO9108760 (1991); Weiner, H. et al., "Methods of treating or preventing autoimmune uveoretinitis in mammals," WO9101333 (1991); Weiner, H. et al., "Method of treating or preventing type 1 diabetes by oral administration of insulin," WO9206704 (1992); Hafler, D. et al., "Bystander suppression of retroviral-associated neurological disease," WO940121 (1994); Weiner, H. et al., "Method of treating rheumatoid arthritis with type II collagen," WO9407520 (1994); Weiner, H. et al., "Methods and compositions for suppressing allograft rejection in mammals," WO9207581 (1992); Wucherpfenning, K. et al., "Multiple sclerosis T-cell receptor," WO9115225 (1991); Weiner, H. et al., "Suppression of proliferative response and induction of tolerance with polymorphic class II mhc allopeptides," WO9320842 (1993); Weiner, H. et al., "Suppression of T-cell proliferation using peptide fragments of myelin basic protein," WO9321222 (1993); and Weiner, H. et al., "Treatment of autoimmune diseases by oral administration of autoantigens," WO9206708 (1992).

Intravenous administration of autoantigens (and fragments thereof containing immunodominant epitopic regions) has been found to induce immune suppression through a mechanism called clonal anergy. Clonal anergy causes deactivation of only immune attack T-cells specific to a particular antigen, the result being a significant reduction in the immune response to this antigen. Thus, the autoimmune response-promoting T-cells specific to an autoantigen, once clonal anergized, no longer proliferate in response to that antigen. This reduction in proliferation also reduces the immune reactions responsible for autoimmune disease symptoms (such as neural tissue damage that is observed in MS). There is also evidence that oral administration of autoantigens (or immunodominant fragments) in a single dose and in substantially larger amounts than those that trigger "active suppression" may also induce tolerance through clonal anergy (or clonal deletion).

A method of treatment has also been disclosed that proceeds by active suppression. Active suppression functions via a different mechanism from that of clonal anergy. This method, discussed extensively in Weiner (1993), involves oral or mucosa administration of antigens specific to the tissue under autoimmune attack. These so called "bystander antigens" cause regulatory (suppressor) T-cells to be induced in the gut-associated lymphoid tissue (GALT), or bronchial associated lymphoid tissue (BALT), or most generally, mucosa associated lymphoid tissue (MALT); MALT includes both GALT and BALT. These regulatory cells are released in the blood or lymphatic tissue and then migrate to the organ or tissue afflicted by the autoimmune disease and suppress autoimmune attack of the afflicted organ or tissue.

The T-cells elicited by the bystander antigen recognize at least one antigenic determinant of the bystander antigen used to elicit them and are targeted to the locus of autoimmune attack where they mediate the local release of certain immunomodulatory factors and cytokines, such as transforming growth factor beta (TGF-$\beta$), interleukin-4 (IL-4), and/or interleukin-10 (IL-10). Of these, TGF-$\beta$ is an antigen-nonspecific immunosuppressive factor in that it suppresses immune attack regardless of the antigen that triggers the attack. (However, because oral or mucosa tolerization with a bystander antigen only causes the release of TGF-$\beta$ in the vicinity of autoimmune attack, no systemic immunosuppression ensues.) IL-4 and IL-10 are also antigen-nonspecific immunoregulatory cytokines. IL-4 in particular enhances Th2 response (i.e., acts on T-cell precursors and causes them to differentiate preferentially into Th2 cells at the expense of Th1 responses). IL-4 also indirectly inhibits Th1 exacerbation. IL-10 is a direct inhibitor of Th1 responses. After orally tolerizing mammals afflicted with autoimmune disease conditions with bystander antigens, increased levels of TGF-$\beta$, IL-4, and IL-10 are observed at the locus of autoimmune attack (Chen, Y. et al., "Regulatory T cell clones induced by oral tolerance: suppression of autoimmune encephalomyelitis," *Science*, 265: 1237-1240, (1994)). The bystander suppression mechanism has been confirmed by von Herrath et al., "Oral insulin treatment suppresses virus-induced antigen-specific destruction of beta cells and prevents autoimmune diabetes in transgenic mice," *J. Clin. Invest.*, 96: 1324-1331, (1996).

Although the induction of tolerance and a bystander effect has been demonstrated for a number of antigens, there remains a need to develop methods for inducing tolerance to E-selectin, and a determination of whether such induction is possible. Furthermore, there remains a need to determine whether E-selectin can be used as a bystander antigen for the induction of tolerance that provides active suppression.

This invention meets these needs by providing a method for inducing tolerance of E-selectin. Furthermore, this invention provides a method for treating stroke by the treatment of E-selectin, apparently through a bystander effect provided by E-selectin tolerance. These and other advantages, benefits, and uses of the present invention will be apparent to those of skill in the art upon a consideration of the present specification.

SUMMARY OF THE INVENTION

In general, the present invention relates to methods for preventing damage to brain tissue resulting from blood vessel obstructions by treatment with E-selectin. The present invention also relates to methods for inducing tolerization to E-selectin. More particularly, the present invention provides a method for reducing stroke-related tissue damage by treating a mammal with E-selectin. Preferably, this treatment induces E-selectin tolerance in the mammal. Another aspect of the invention is a method for inducing E-selectin tolerance in a mammal through intranasal administration of E-selectin, preferably including booster administrations.

This invention is especially useful in treatment of patients with a known increased risk of stroke. Such patients would include, for example, persons with high blood pressure (especially severe high blood pressure or high blood pressure not controllable with conventional drug treatment), persons with a family history of stroke, persons with one or more previous strokes, diabetes, hypercholesterolemia, and the like. The present method can also be used for treatment of patients scheduled to undergo drug treatments or surgical procedures that might increase the risk of stroke. The present methods can, however, be used with individuals without known increased risk to stroke.

DESCRIPTION OF THE PREFERRED EMBODIMENTS

Figure 1:
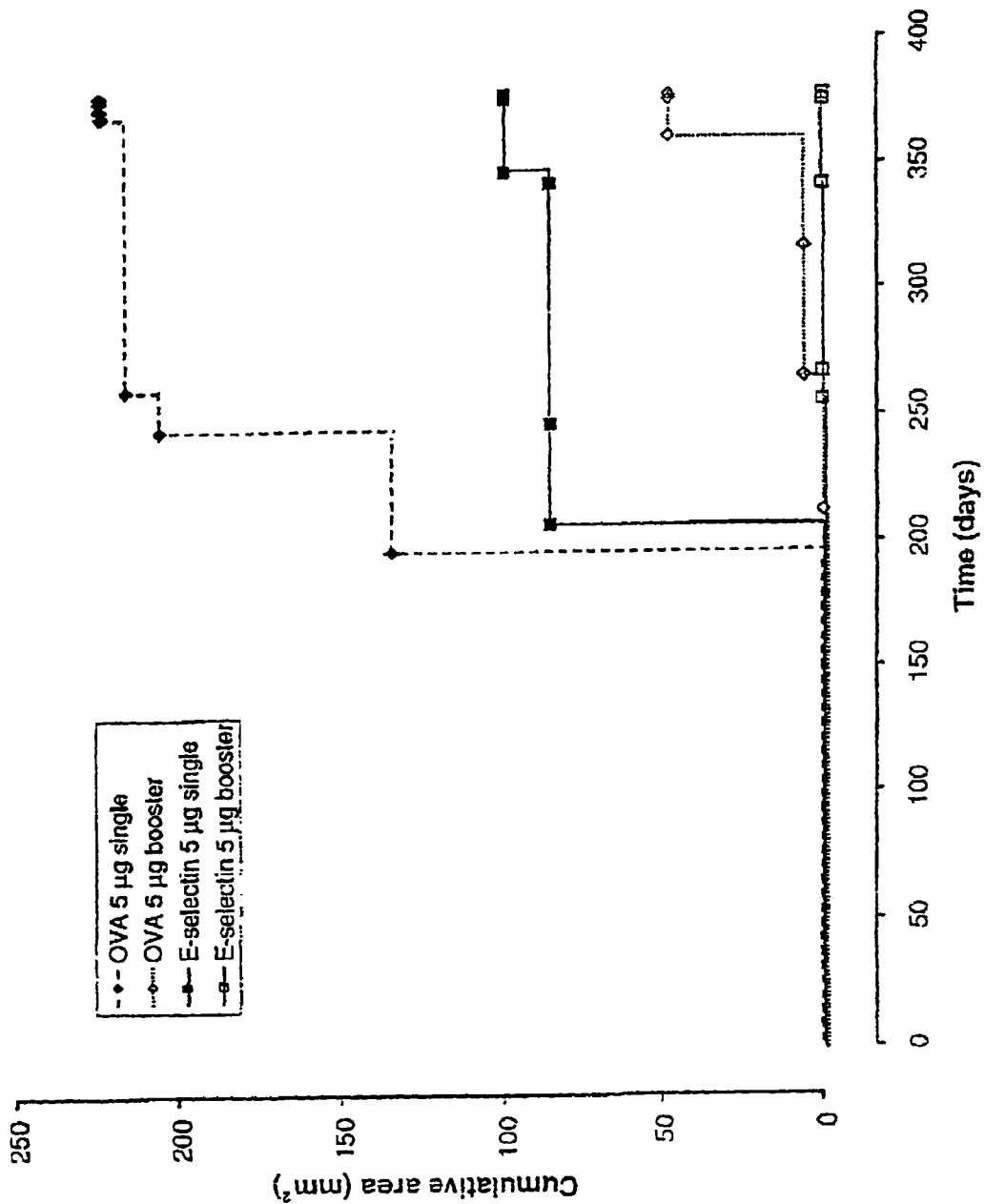
FIG. 1 is a graph of cumulative infarct and hemorrhage areas (in mm$^2$) over time (days). Shaded diamonds, ovalbumin 5 µg single regimen; open diamonds, ovalbumin 5 µg regimen with boosters; shaded squares, E-selectin 5 µg single regimen; open squares E-selectin 5 µg regimen with boosters.
Figure 2:
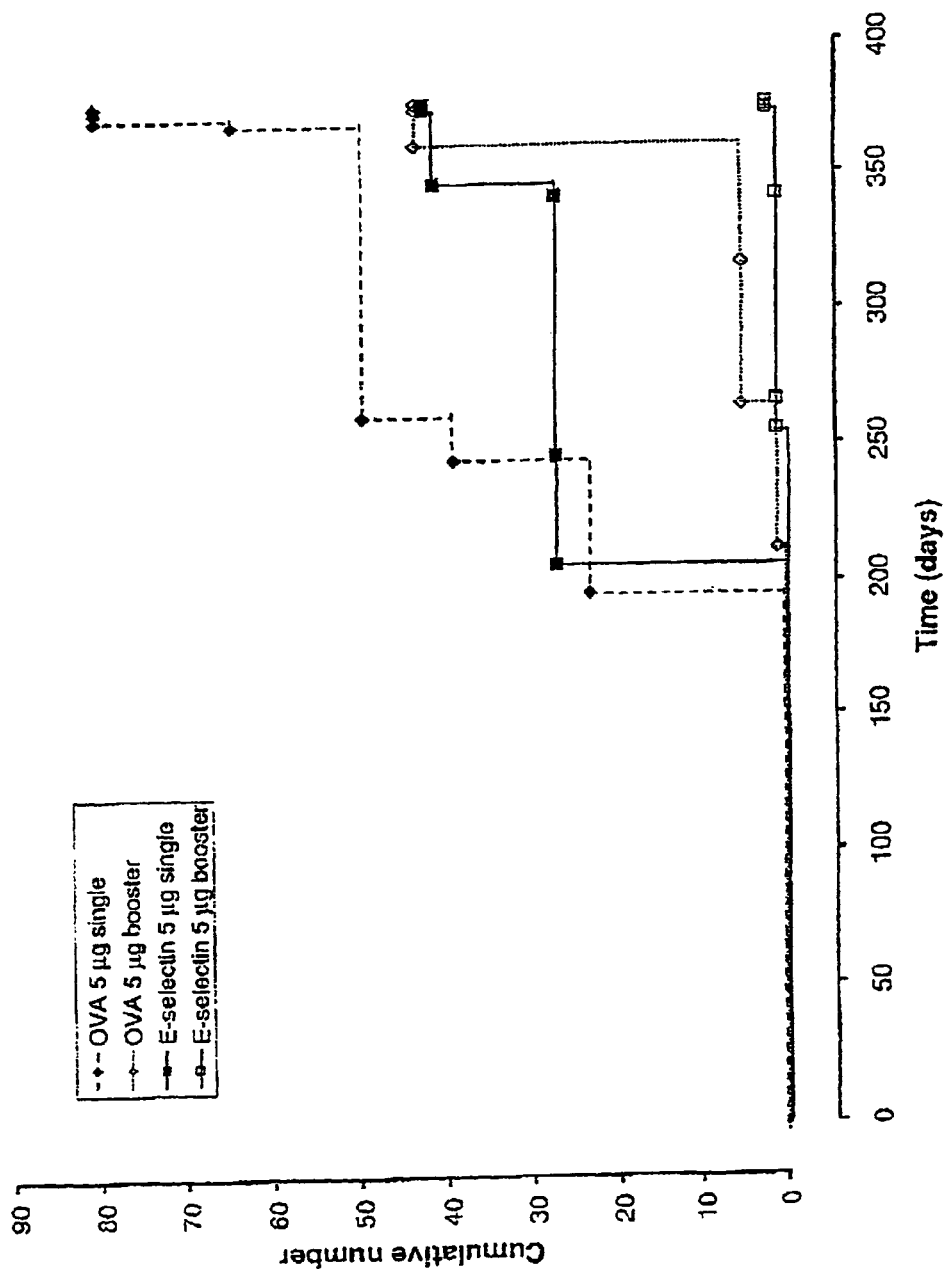
FIG. 2 is a graph of cumulative number of infarcts and hemorrhages over time (days). Shaded diamonds, ovalbumin 5 µg single regimen; open diamonds, ovalbumin 5 µg regimen with boosters; shaded squares, E-selectin 5 µg single regimen; open squares, E-selectin 5 µg regimen with boosters.
Figure 3:
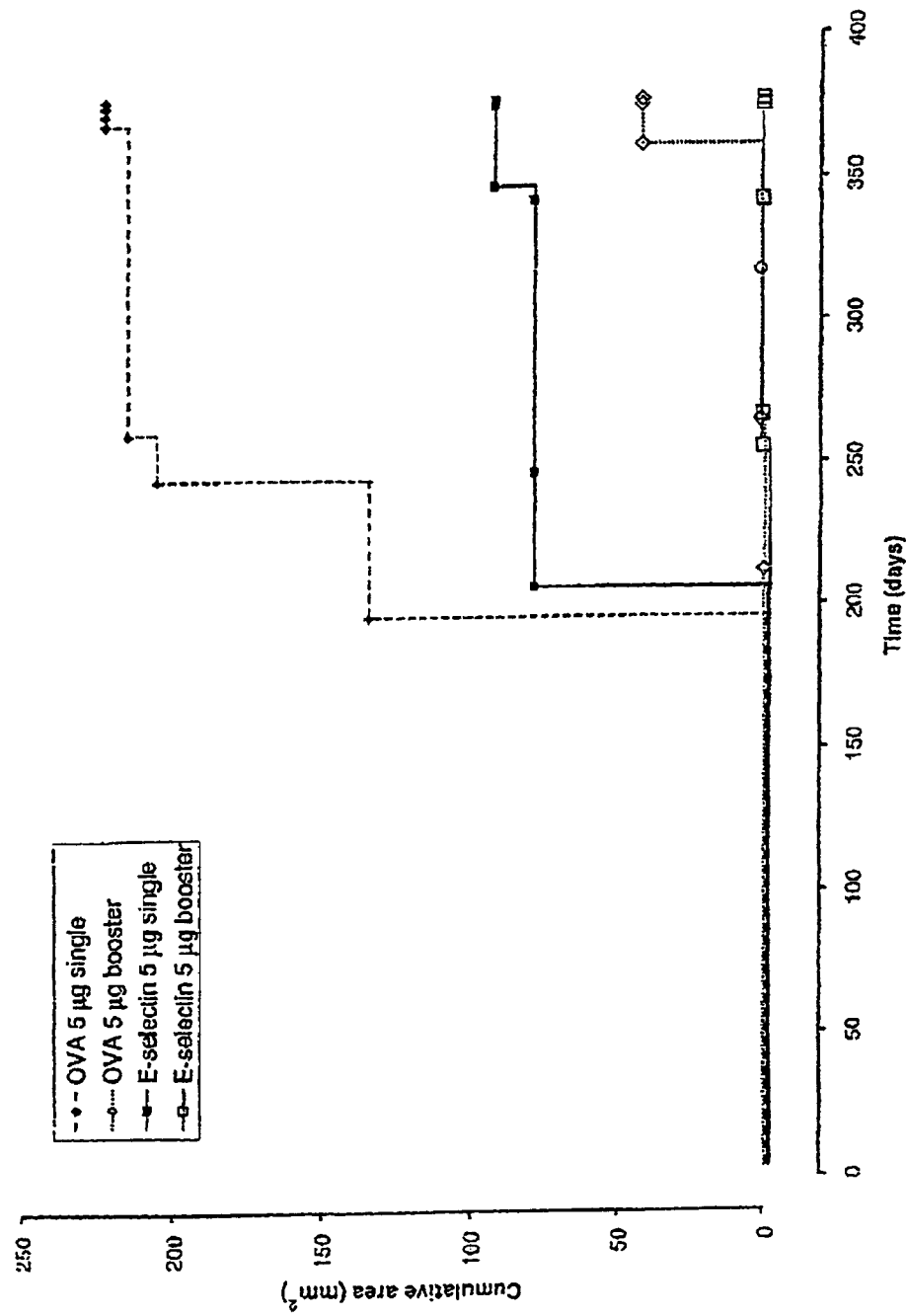
FIG. 3 is a graph of cumulative infarct area (in mm$^2$) over time (days). Shaded diamonds, ovalbumin 5 µg single regimen; open diamonds, ovalbumin 5 µg regimen with boosters; shaded squares, E-selectin 5 µg single regimen; open squares, E-selectin 5 µg regimen with boosters.
Figure 4:
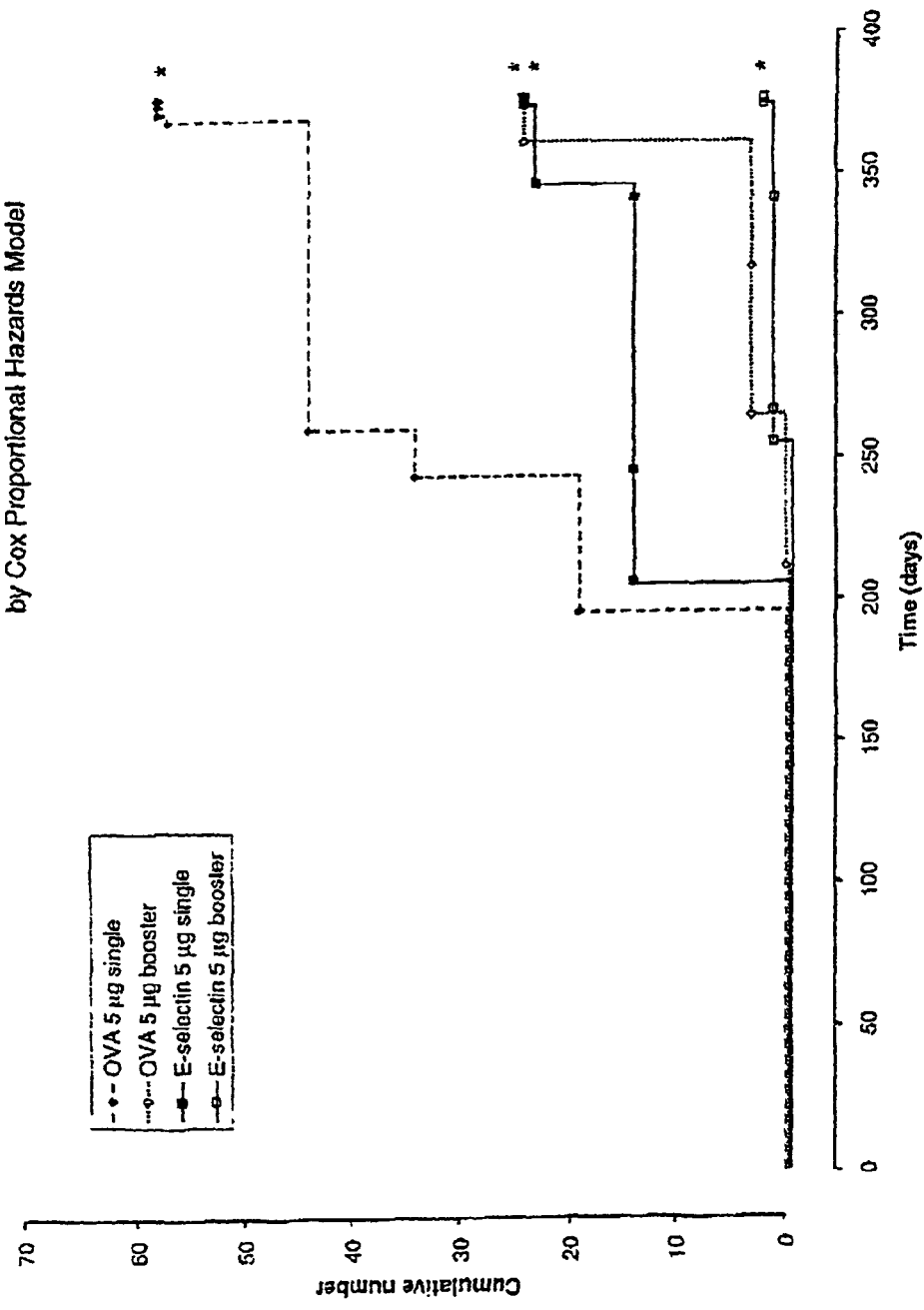
FIG. 4 is a graph of cumulative number of infarcts over time (days). Shaded diamonds, ovalbumin 5 µg single regimen; open diamonds, ovalbumin 5 µg regimen with boosters; shaded squares, E-selectin 5 µg single regimen; open squares, E-selectin 5 µg regimen with boosters. Asterisks indicate data points where the values for ES groups are statistically decreased (p<0.0001) using a Cox Proportional Hazards Model over values obtained for control groups.
Figure 5:
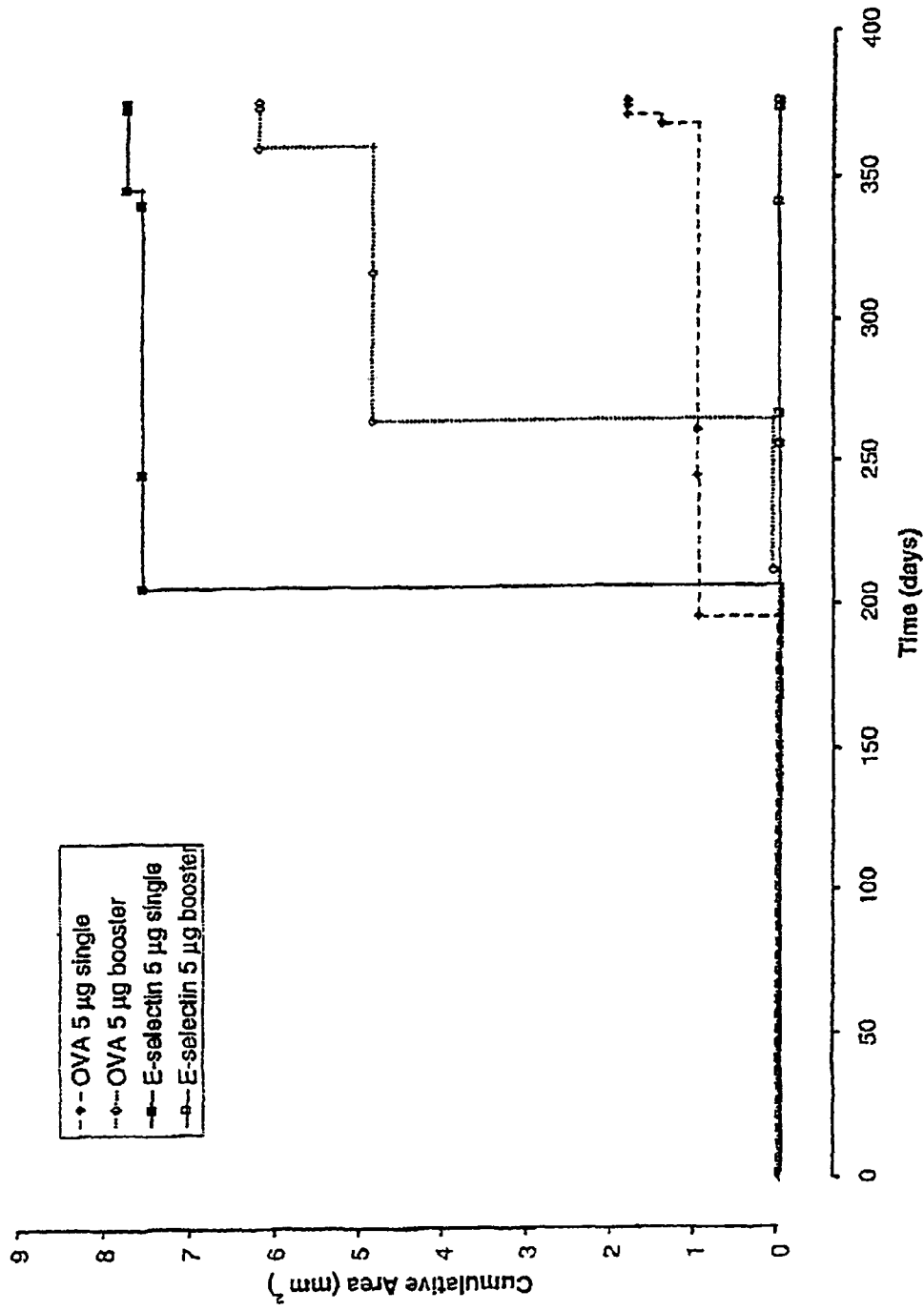
FIG. 5 is a graph of cumulative intraparenchymal hemorrhage areas (in mm$^2$) over time (days). Shaded diamonds, ovalbumin 5 µg single regimen; open diamonds, ovalbumin 5 µg regimen with boosters; shaded squares, E-selectin 5 µg single regimen; open squares, E-selectin 5 µg regimen with boosters.
Figure 6:
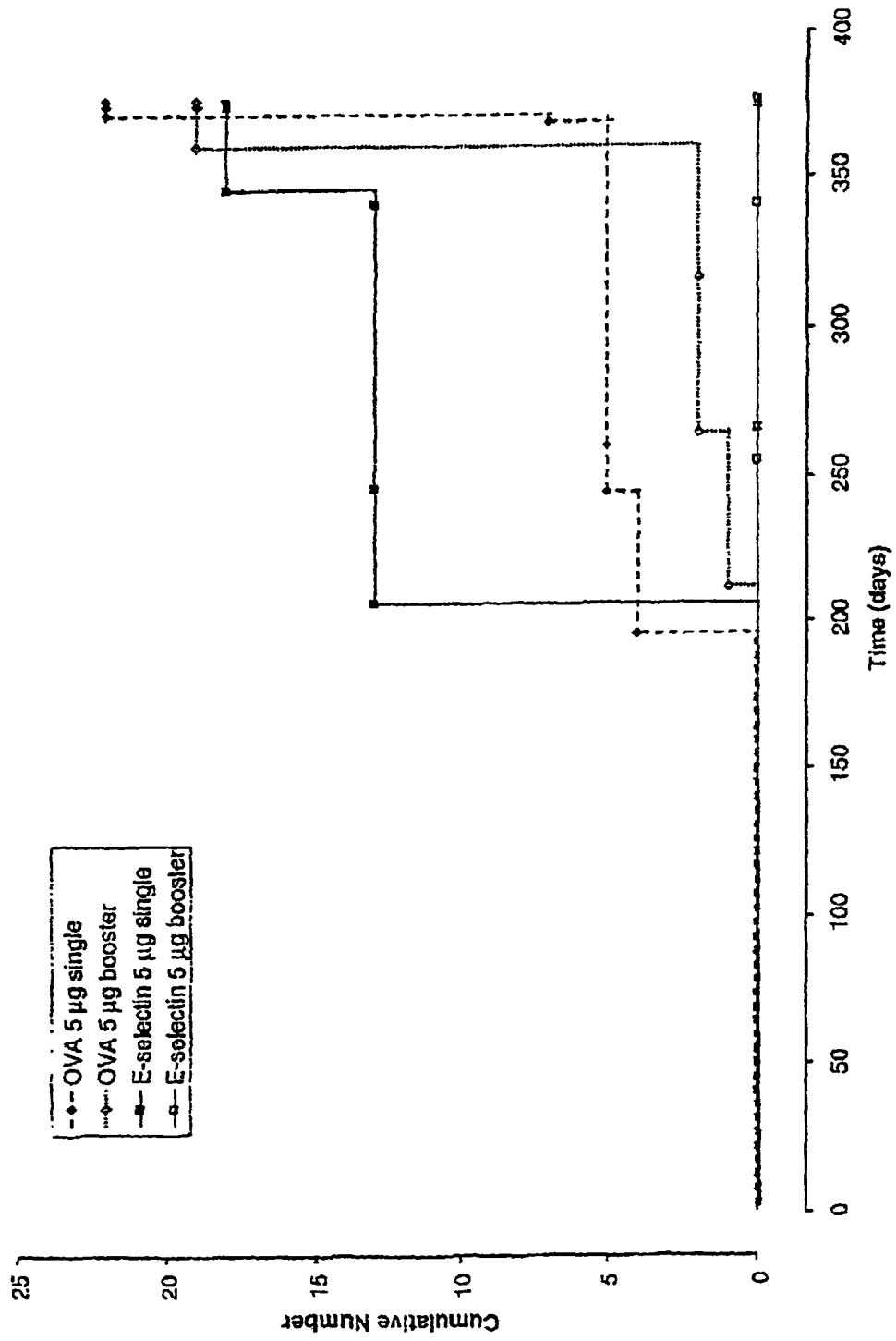
FIG. 6 is a graph of cumulative number of intraparenchymal hemorrhages over time (days). Shaded diamonds, ovalbumin 5 µg single regimen; open diamonds, ovalbumin 5 µg regimen with boosters; shaded squares, E-selectin 5 µg single regimen; open squares, E-selectin 5 µg regimen with boosters.

Methods for preventing or treating strokes with E-selectin. In one aspect, the invention is a method for preventing strokes or reducing tissue damage caused by a stroke in a patient. The method comprises administering E-selectin to the patient. Preferably, E-selectin is administered in a manner that induces tolerance, most preferably bystander-effect tolerance.

E-selectin (also known as ELAM-1, CD62, and CD62E) is a cytokine inducible cell surface glycoprotein cell adhesion molecule that is found exclusively on endothelial cells. Structurally, E-selectin belongs to a family of adhesion molecules termed "selecting" that also includes P-selectin and L-selectin (see reviews in Lasky, 1992 and Bevilacqua and Nelson, 1993). These molecules are characterized by common structural features such as an amino-terminal lectin-like domain, an epidermal growth factor (EGF) domain, and a discrete number of complement repeat modules (approximately 60 amino acids each) similar to those found in certain complement binding proteins.

Sources of E-selectin that can be used with the current invention include E-selectin that has been substantially purified from natural sources, recombinant E-selectin produced in procaryotic or preferably eukaryotic host cells by methods well-known in the art, and fragments of E-selectin. Furthermore, E-selectin can be replaced in the current invention by a small organic molecule or a small peptide with a structure that mimics that of a portion of, preferably an immunoreactive portion of E-selectin is used. As used herein, "substantially pure" refers to a purity that allows for the effective use of E-selectin for the treatment of stroke or induction of tolerance.

Preferably, E-selectin for the current invention is from the same species to which it is being administered. However, as illustrated in the attached Examples, E-selectin is effective in at least some instances in species other than that from which it originated. For example, human E-selectin is effective when administered to rats in accordance with the methods of the current invention. Human E-selectin is comprised of 589 amino acids and has a molecular weight of 64 kDa. Nucleic acids encoding human E-selectin have been cloned and sequenced. (Bevilacqua, M. P. 1989). In one embodiment, the source of E-selectin used for the current invention is recombinant human E-selectin.

E-selectin tolerance induced by the bystander antigens of this invention is dose-dependent over a broad range of dosages. However, there are minimum and maximum effective dosages which will, of course, vary depending on the method of administration. In other words, active suppression of the clinical and histological changes accompanying or causing a stroke occur within a specific dosage range, which, however, varies depending on the organism receiving the dosage, the route of administration, whether E-selectin is administered in conjunction with other co-stimulatory molecules, and the specific regimen of E-selectin administration. For example, for oral administration E-selectin is generally administered in dosages ranging from about 0.005 and 500 mg/day., more preferably about 0.05 to 50 mg/day. Preferred oral dosages are from 0.5 ug to 50 mg per administration.

Many delivery routes are known in the art for inducing bystander-effect tolerance. These routes include mucosa routes such as, but not limited to, enteral, oral, inhalable, and intranasal routes. For the current invention E-selectin tolerance is preferably induced by dropwise or spray application of E-selectin intranasally.

E-selectin formulations for use with the methods of the present invention may comprise inert constituents including pharmaceutically-acceptable carriers, diluents, solubilizing agents, emulsifying agents, salts, and the like, as is well-known in the art. Preferred E-selectin formulations are intranasal formulations including normal saline solutions, such as, for example, isotonic and physiologically buffered saline solutions and phosphate-buffered saline (PBS) solutions. The total volume of the intranasal formulations is typically less than 1 milliliter, preferably less than 100 µl. For oral or enteral E-selectin formulations for use with the present invention, tablets may be formulated in accordance with conventional procedures employing solid carriers well-known in the art. Capsules employed for oral formulations to be used with the methods of the present invention may be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982.

Examples of solid carriers include starch, sugar, bentonite, silica, and other commonly used carriers. Further non-limiting examples of carriers and diluents which may be used in the formulations of the present invention include saline, syrup, dextrose, and water.

E-selectin can also be administered in an aerosol or inhaled form. Examples of formulations for tolerizing agents administered by inhalation are provided in Weiner, H. et al., "Improved treatment of autoimmune diseases by aerosol administration of auto antigens," WO9108760 (1991). The antigens can be administered as dry powder particles or as an atomized aqueous solution suspended in a carrier gas (e.g., air, $N_2$, and the like).

Dry aerosol in the form of finely divided solid particles of E-selectin that are not dissolved or suspended in a liquid can also be used in the practice of the present invention. E-selectin formulations may be in the form of dusting powders and comprise finely divided particles having an average particle size of between about 1 and 5 microns, preferably between 2 and 3 microns. Finely divided particles may be prepared by pulverization and screen filtration using techniques well known in the art. The particles may be administered by inhaling a predetermined quantity of the finely divided or powdered material. The E-selectin formulations of the present invention may also be administered in the form of an aerosol spray using, for example, a nebulizer such as those described in U.S. Pat. No. 4,624,251 issued Nov. 25, 1986; U.S. Pat. No. 3,703,173 issued Nov. 21, 1972; U.S. Pat. No. 3,561,444 issued Feb. 9, 1971; and U.S. Pat. No. 4,635,627 issued Jan. 13, 1971. Other systems of aerosol delivery, such as the pressurized metered dose inhaler (MDI)

and the dry powder inhaler (see, e.g., Newman, S. P. in Aerosols and the Lung, Clarke, S. W. and Davia, D. eds. pp. 197-224, Butterworths, London, England, 1984) can be used when practicing the present invention.

One particularly useful animal model for the analysis of E-selectin formulations and their effectiveness in treating or preventing stroke is the stroke-prone and spontaneously hypertensive SHR-SP rat (Okamoto, K. et al., "Establishment of the stroke-prone spontaneously hypertensive rat (SHR)," *Circ. Res.* (Suppl.) 34, 35: 1 (1974)). SHR-SP rats are available upon request from professor Yukio Yamori, Graduate School of Human and Environmental Studies, Kyoto University, Yoshida Nihonmatsu-cho, Sakyo-ku, Kyoto, 606-8316, Japan. SHR-SP rats typically die of early-onset cardiovascular disease, sometimes as early as 14 weeks of age, although some SHR-SP rats live to more than 56 weeks of age. Frequently, the cardiovascular disease manifests as a stroke in these rats. The occurrence of a stroke in these rats is diagnosed by measuring behavioral status that could be divided into 4 patterns: no abnormalities (grade 1), irritable (grade 2), lethargic (grade 3), akinetic (grade 4) (Yamori, U. et al., Japanese Criculation Journal 46: 274 (1982)).

The brains of SHR-SP rats at the time of death, typically contain numerous infarcts and intraparenchymal hemorrage areas that can be counted and measured through microscopal analysis of brain sections. The effectiveness of an E-selectin formulation can be determined by comparing infarct and intraparenchymal hemorrhage number and area of SHR-SP rats that have been treated with a test E-selectin formulation administered on a booster regime with those that have been treated with control formulations consisting of only carrier components, non-specific antigens (e.g., ovalbumin), or E-selectin on a single tolerization rather than a booster schedule. An example of this strategy is disclosed in the Examples section of this specification.

The optimum dosage of E-selectin is one generating the maximum beneficial effect on brain tissue damage caused by thrombosis assessed as described above. An effective dosage causes at least a statistically or clinically significant attenuation of at least one marker, symptom, or histological evidence characteristic of stroke, such as those described above. Stabilization of symptoms or tissue damage, under conditions wherein control patients or animals experience a worsening of symptoms or tissue damage, is one indicator of efficacy of a suppressive treatment.

Ascertaining the effective dosage range as well as the optimum amount of E-selectin is determined using conventional methods and the teachings of the present application. For example, dosages for mammals and human dosages can be determined by beginning with a relatively low dose (e.g., 1 microgram) and progressively increasing it while measuring appropriate responses (e.g., number of TGF-beta, IL-4, and/or IL-10 secreting cells; number and activation of immune attack T-cells in the blood (e.g., by limiting dilution analysis and ability to proliferate); and/or disease severity). The optimum dosage generates the maximum amount of prevention of strokes or the maximum protection from tissue damage in the brain caused by thrombosis while minimizing undesirable side effects. Potential side effects include the generation of pathogenic autoantibodies (Hu, W. et al., "Experimental mucosal induction of uveitis with the 60-kDa heat shock protein-derived peptide 336-351," *Eur. J. Immunol.* 28: 2444 (1998); Genain C. P., et al., "Late complications of immune deviation therapy in a nonhuman primate," *Science* 274: 2054 (1996)) or a cytotoxic T lymphocyte response that induces autoimmunity (Blanas E., et al., "Induction of autoimmune diabetes by oral administration of autoantigen," *Science* 274: 1707 (1996)).

An effective dosage causes at least a statistically or clinically significant attenuation of at least one manifestation of thrombosis in the skull cavity such as, for example, the number or area of brain infarcts, the number or area of brain intraparenchymal hemorrhage, the occurrence rate or time to onset of stroke, and the like. The maximum effective dosage of a bystander antigen in humans can be ascertained by testing progressively higher dosages clinical trials starting with a relatively low dosage, for example 0.5 µg per administration.

Preferred dosages for intranasal instillations are from 0.5 to 50 mg per administration, preferably for humans approximately from 5 µg to 5 mg per administration. For rats, one preferred dosage is 5 µg per administration. Preferred aerosol pharmaceutical formulations may comprise, for example, a physiologically-acceptable buffered saline solution containing between about 1 mg and about 300 mg of E-selectin.

Ascertaining the optimum regimen for administering E-selectin is determined in light of the information disclosed herein and well known information concerning administration of bystander antigens and autoantigens. Routine variation of dosages, combinations, and duration of treatment is performed under circumstances wherein the effects of such variations on the organism can be measured.

E-selectin is preferably used in the practice of this invention using a series of administrations. Typically these administrations are spaced apart over a period of 1 to 2 weeks. For example and as further detailed in the Examples, E-selectin can be administered in five intranasal administrations over a two week period. Preferably, this protocol involves administering E-selectin every other day for ten days. Preferably, the administration regimen is repeated in booster administrations which are generally administered several weeks apart. In one preferred embodiment, booster administrations are given after every three weeks. Booster administrations may include a series of administrations, as described above for initial administrations.

Cytokine and non-cytokine synergists can be used in conjunction with E-selectin in the present invention to enhance the effectiveness of E-selectin tolerization. Administration "in conjunction with" encompasses simultaneous and sequencial administration, as well as administration in combined form or separately. Oral and parenteral use of cytokine synergists (Type I interferons) has been described in Hafler, D. A. et al., "Treatment of autoimmune disease using oral tolerization and/or type 1 interferon," WO9527499 (1995). Administration of Th2 enhancing cytokines is described in Weiner H. L., et al., "Treatment of autoimmune disease using oral tolerization and/or Th2-enhancing cytokines," WO95275000(1995). For example, IL-4 and IL-10 can be administered in the manner described in Weiner et al. Id.

Non-limiting examples of non-cytokine synergists for use in the present invention include bacterial lipopolysaccharides from a wide variety of gram negative bacteria such as various subtypes of *E. coli* and Salmonella (LPS, Sigma Chemical Co., St. Louis, Mo.; Difco, Detroit, Mich.; BIO-MOL Res. Labs., Plymouth, Pa.), Lipid A (Sigma Chemical Co., St. Louis, Mo.; ICN Biochemicals, Cleveland, Ohio; Polysciences, Inc., Warrington, Pa.); immunoregulatory lipoproteins, such as peptides covalently linked to tripalmitoyl-S-glycarylcysteinyl-seryl-serine (P.sub.3 C55) which can be obtained as disclosed in Deres, K. et al. (*Nature*, 342: 561-564, "In vivo priming of virus-specific cytotoxic T lymphocytes with synthetic lipopeptide vaccine," 1989) or "Braun's" lipoprotein from *E. coli* which can be obtained as disclosed in Braun, V., Biochim. Biophys. Acta 435: 335-337, 1976; and cholera toxin β-chain (CTB) the synergist ability of which has been described (though not in connection with abatement of autoimmune reaction) by Sun, J-B et al., "Cholera toxin B subunit: an efficient transmucosal carrier-delivery system for induction of peripheral immunological tolerance," *Proc. Natl. Acad. Sci.* (USA) 91: 10795 (1994). The effective dosage range for noncytokine synergists for mammals is from about 15 ng to about 15 mg per kg weight and preferably 300 ng-12 mg per kg weight. The effective dosage range for oral Type I interferon for mammals is from 1,000-150,000 units with no maximum effective dosage having been discerned. Another active compound that may be useful in combination with E-selectin is methotrexate which is known to cause a marked Th2 immune deviation with greatly increased IL-4 secretion when given on a pulse regimen (Weiner et al., "Treatment of Autoimmune Disease Using Tolerization in Combination with Methotrexate," U.S. Pat. No. 5,935,577 (1999).

Ascertaining the optimum regimen for administering E-selectin and/or the co-stimulatory molecule is determined in light of the information disclosed herein and well known information concerning administration of bystander antigens and autoantigens. Routine variation of dosages, combinations, and duration of treatment is performed under circumstances wherein the effects of such variations on the organism can be measured. The co-stimulatory agent is preferably administered within 24 hours of administration of E-selectin. More preferably, it is administered at the same time as E-selectin. Most preferably, both are administered in a combined oral formulation.

Not to be limited by theory, this invention is based on the hypothesis that activation of the luminal surface of endothelium in a vascular segment by proinflammatory cytokines such as tumor necrosis factor-alpha and interluekin-1-beta is a prerequisite for the development of thrombosis or the evolution of inflammatory vessel damage in that segment. The general approach involves exposing lymphocytes in bronchial-associated lymphoid tissue (BALT) and perhaps gut-associated lymphoid tissue (GALT) to an adhesion molecule antigen to produce tolerized lymphocytes. The antigen is instilled intranasally. The tolerized lymphocytes undergo "immune deviation," thereby synthesizing and releasing transforming growth factor-beta (TGFβ; a cytokine that causes paracrine "bystander suppression" of proinflammatory cytokine production) when the same antigen is encountered again. The antigen is E-selectin, an adhesion molecule that is only expressed on the endothelial surface in vascular segments that have become activated. The essence of this approach is, therefore, to program autologous lymphocytes to become mobile monitors that provide continuous surveillance of vessels. When they encounter E-selectin in an activated segment they bind to that segment and become stimulated to produce TGFβ. The TGFβ then suppresses production of proinflammatory cytokines, reduces endothelial thrombogenecity and minimizes vessel injury. After a single antigen exposure, tolerance of lymphocytes lasts for a period of weeks and long-term maintenance of the tolerant state requires repeated booster exposures to the antigen.

Furthermore, the current invention provides methods of reducing the likelihood of a stroke by a mechanism that may include specifically reducing intracranial hemorrhage. Although not wishing to be limited by theory, this conclusion is based on the following considerations related to intracranial hemorrhage and endoglin gene polymorphisms.

Mutations of the endoglin gene have been associated with intracranial hemorrhage in patients (Alberts, M. J. et al., "Endoglin gene polymorphism as a risk factor for sporadic intracerebral hemorrhage," Ann. Neurol., 41: 683 (1997)). Endoglin appears to bind TGF-β and subsequently plays a role in vascular maintenance and development. Imparirment of endoglin function appears to diminish the response of the endothelium to TGF-β resulting in an increased tendency to hemorrhage. E-selectin tolerization also appears to increase the number of TGF-β positive lymphocytes and may increase the release of TGF-β in vessel segments that are becoming activated, as described above. This would be predicted to reduce the likelihood of hemorrhage in the presence of endoglin. This is potentially relevant to the observed elimination of intracranial hemorrhage in the group that received E-selectin tolerization and booster tolerization, as described in Examples section below.

In another aspect, the current invention provides a method for mitigating brain tissue damage following a stroke by administering E-selectin to a patient immediately after, or preferably before occurrence of the stroke. Preferably, E-selectin is administered in a manner that induces tolerance, as described below, most preferably bystander-effect tolerance. Considerations regarding E-selectin sources, doses, delivery routes, formulations, and the like, are described above for methods of preventing a stroke. As shown in the attached Examples, not only does E-selectin administration significantly reduce the number of infarcts formed in a stroke-prone rat model, the infarcts that form are significantly smaller in size than control infarcts. Therefore, tolerance to E-selectin appears to minimize brain tissue damage in animals that have a stroke while they are in a state of E-selectin tolerance.

Method for Inducing E-Selectin Tolerance. One aspect of the current invention is a method for inducing E-selectin tolerance in a host. The method comprises intranasal administration of E-selectin. In one preferred embodiment the protocol consists of booster intranasal administrations of E-selectin.

In one embodiment, E-selectin tolerance is induced by a five by two administration protocol of five intranasal administrations of E-selectin over a period of two weeks. In a most preferred embodiment, this five by two administration is repeated at least once. Most preferably, this booster regimen is repeated every three weeks for the life of the organism.

Preferred dosages, E-selectin sources, formulations, dosage volumes, regimens, and methods for analyzing results aimed at optimizing these considerations for intranasal instillations for inducing E-selectin tolerance are similar to those described above for the use of E-selectin administration in stroke prevention. For example, the preferred dosages range from 0.5 μg to 50 mg per administration, preferably for humans approximately from 5 μg to 5 mg per administration. Optimization of the dosage necessary for immune suppression involves no more than routine experimentation, given the guidelines disclosed herein.

The current aspect of the invention for inducing E-selectin tolerance has many utilities. For example, it can be used in preventing and treating strokes and other forms of vascular disease such as coronary artery disease. Additionally, it can be used in treating disorders in which E-selectin has been determined, or may be determined, to play a role, such as, for example, lung injury, psoriasis, contact dermatitis, inflammatory bowel disease, arthritis, and the like. (See, e.g., Washington R., et al., "Expression of immunologically relevant endothelial cell activation antigens on isolated central nervous system microvessels from patients with multiple sclerosis," *Ann. Neurol.* 35: 89 (1994); Bevilacqua (1989); Bevilacqua and Nelson, "Selectins," *J. Clin. Invest.* 91: 379 (1993); Koch, et al., "Immunolocalization of endothelial and leukocyte adhesion molecules in human rheumatoid and osteoarthritic synovial tissues," *Lab Invest.* 64: 313 (1991); Mulligan, et al., "Role of endothelial-leukocyte adhesion molecule 1 (ELAM-1) in neutrophil-mediated lung injury in rats," *J. Clin. Invest.* 88: 1396 (1991); and Mulligan, et al., "Protective effects of oligosaccharides in P-selectin-dependent lung injury," *Nature* 364: 149 (1993)).

Assessment of the effect of E-selectin formulations on an immune response to E-selectin can be made, for example, by determining diminution in certain inflammation markers, such as the number of activated T-cell clones directed against activated vascular tissue. Immunological tolerance can be measured by a number of methods that are well-known in the art. In one preferred embodiment, delayed type hypersensitivity (DTH) response can measured in animals by injecting E-selectin into, for example, the footpad of an organism to be analyzed and then administering a booster injection, for example into a footpad or an ear, at a later time, typically more than 1 week later, most preferably 2 weeks later. DTH reactions can be measured after the elicitation injection as the increase in swelling at the site of the antigen rechallenge. Footpad or ear swelling can be measured at, for example, 0, 24 and 48 hr after challenge.

Methods for analyzing effects of E-selectin tolerance on stroke occurrence or stroke-related damage using stroke-prone rats is discussed above and in the Examples section. This method is useful as an indirect measure of the effectiveness of a particular dosage, formulation, and protocol on inducing E-selectin tolerance through intranasal administration of E-selectin.

The various publications, issued patents, published patent applications, and the like cited in this present application are hereby incorporated by reference. The following examples describe and illustrate the methods and compositions of the invention. These examples are intended to be merely illustrative of the present invention, and not limiting thereof in either scope or spirit. Those of skill in the art will readily understand that variations of the materials used in, and the conditions and processes of, the procedures described in these examples can be used.

EXAMPLE 1

Reduction of brain infarcts by administration of E-selectin. The effects of administration of E-selectin on infarcts of the brains of stroke-prone rats was analyzed. Male and female stroke-prone and spontaneously hypertensive (SHR-SP) 8-10 week-old rats were obtained from the NIH colony. (Okamoto (1974)). At 11 weeks of age, E-selectin-(soluble human E-selectin: human E-selectin lectin, EGF, CR1, CR2 domains, myc peptide tail) ovalbumin or vehicle (PBS) were administered intranasally. Purified human E-selectin was obtained from Protein Design Laboratories (Fremont, Calif.).

E-selectin and control preparations were administered in the following manner: SHR-SP rats were divided into three groups: (1) a saline (PBS) control group, (2) an E-selectin administration group (ES group), and (3) an ovalbumin (OVA) administration group (OVA group). In addition, ES and OVA groups were divided into single (non-booster) and repetitive (booster) administration groups. For the control group, 20 μl of phosphate-buffered saline (PBS) was administered into each nostril every other day for 10 days for a total of 5 administrations. For the ES non-booster group, 2.5 μg E-selectin in 20 μl PBS was administered into each nostril every other day for 10 days for a total of 5 administrations. For the ES booster group, an initial 2.5 μg of E-selectin in 20 μl PBS was administered as above for the non-booster group; additionally, 2.5 μg of E-selectin in 20 μl of PBS was administered intranasally into each nostril every other day for 10 days (3 weeks after the first E-selectin course) and repeated every 3 weeks until the animals were sacrificed. For the OVA non-booster group, 2.5 μg ovalbumin in 20 μl PBS was administered into each nostril every other day for 10 days for a total of 5 administrations. For the OVA booster group, an initial 2.5 μg of ovalbumin in 20 μl PBS was administered into each nostril as above for the non-booster group; additionally, 2.5 μg of ovalbumin in 20 μl of PBS was administered intranasally into each nostril every other day for 10 days (3 weeks after the first ovalbumin course) and repeated every 3 weeks until the animals were sacrificed.

The rats were evaluated for physical and neurological signs of stroke. These evaluations included an assessment of excitement (i.e., piloerection, hyperkinesis), hyperirratibility (i.e., jumping, trying to escape), behavioral and psychological depression (i.e., hypokinesis, hyposthenia, hypotenia, hyporesponsiveness), motion disturbance (i.e., transient episode of repetitiv lifting of paws, ataxia, paresis, paralysis), and late symptoms observed near the time of death (i.e., apathy, coma, urinary incontinence). The rats were also monitored by measuring arterial blood pressure, body weight, heart weight, and arterial blood gas using methods know in the art.

Infarcts were evaluated in the following manner. When animals showed signs of cardiac failure, kidney failure, or stroke, they were perfused and their brains were removed for histology and image processing. Sections from 8 predetermined stereotactic levels were cut from each brain (total of 240 sections). The number and area of infarcts or hemorrhages were determined for each section from each animal. Statistical significance of E-selectin administrations was determined by comparing E-selectin groups to control groups by a Cox Proportional Hazards Model.

The animals lived for variable periods from 14 weeks to the termination of the experiment at 56 weeks. Deaths were caused by heart failure and kidney failure secondary to severe hypertension (mean systolic blood pressure 215 mm Hg), as well as by strokes. Average age at time of death and average systolic blood pressure did not differ among the experimental groups.

The experimental group of animals which received E-selectin maintained with booster administrations had a statistically significant reduction in the frequency and area of infarcts compared to control groups ($p<0.0001$) (FIGS. 1-7). Mean area of infarcts decreased from between about 6.873 $mm^2$ to about 27.718 $mm^2$ in control and single administration E-selectin groups to about 0.002 $mm^2$ in the E-selectin booster group (i.e., a greater than 99% reduction; see Tables I-IV, FIGS. 1 and 3). Mean number of infarcts decreased from about 3.0 to about 7.3 for control and single administration E-selectin groups to about 0.3 in E-selectin booster groups (i.e., a greater than 91% reduction; see Tables I-IV, FIGS. 2, and 4). Intraparenchymal hemorrhages were absent from the E-selectin booster group, but were present at an average number of from about 3.2 to about 2.3 per brain section analyzed in control and single E-selectin administration groups (see Tables I-IV and FIGS. 1, 2, 5, and 6).

TABLE I

Group OVA Data

| Sample (sex) | Infarcts Number | Infarcts Area (mm²) | Intraparenchymal Hemorrhage Number | Intraparenchymal Hemorrhage Area (mm²) |
|---|---|---|---|---|
| 1 (female) | 13 | 6.966 | 2 | 0.439 |
| 2 (female) | 0 | 0 | 0 | 0 |
| 3 (female) | 1 | 0.062 | 15 | 0.390 |
| 4 (female) | 19 | 133.850 | 4 | 0.950 |
| 5 (male) | 15 | 70.559 | 1 | 0.021 |
| 6 (male) | 10 | 10.308 | 0 | 0 |
| 7 (female) | 0 | 0 | 0 | 0 |
| 8 (female) | 0 | 0 | 0 | 0 |
| Mean | 7.3 | 27.718 | 2.8 | 0.225 |

TABLE II

Group OVAb Data

| Sample (sex) | Infarcts Number | Infarcts Area (mm²) | Intraparenchymal Hemorrhage Number | Intraparenchymal Hemorrhage Area (mm²) |
|---|---|---|---|---|
| 1 (female) | 0 | 0 | 0 | 0 |
| 2 (male) | 3 | 0.734 | 1 | 4.784 |
| 3 (female) | 21 | 40.502 | 17 | 1.372 |
| 4 (female) | 0 | 0 | 0 | 0 |
| 5 (female) | 0 | 0 | 1 | 0.063 |
| 6 (female) | 0 | 0 | 0 | 0 |
| Mean | 4.0 | 6.873 | 3.2 | 1.037 |

TABLE III

Group ES Data

| Sample (sex) | Infarcts Number | Infarcts Area (mm²) | Intraparenchymal Hemorrhage Number | Intraparenchymal Hemorrhage Area (mm²) |
|---|---|---|---|---|
| 1 (female) | 0 | 0 | 0 | 0 |
| 2 (male) | 0 | 0 | 0 | 0 |
| 3 (female) | 9 | 13.488 | 5 | 0.177 |
| 4 (female) | 14 | 77.909 | 13 | 7.553 |
| 5 (female) | 0 | 0 | 0 | 0 |
| 6 (female) | 1 | 0.012 | 0 | 0 |
| 7 (male) | 0 | 0 | 0 | 0 |
| 8 (male) | 0 | 0 | 0 | 0 |
| Mean | 3.0 | 11.426 | 2.3 | 0.966 |

TABLE IV

Group ESb Data

| Sample (sex) | Infarcts Number | Infarcts Area (mm²) | Intraparenchymal Hemorrhage Number | Intraparenchymal Hemorrhage Area (mm²) |
|---|---|---|---|---|
| 1 (male) | 0 | 0 | 0 | 0 |
| 2 (female) | 0 | 0 | 0 | 0 |
| 3 (female) | 0 | 0 | 0 | 0 |
| 4 (female) | 0 | 0 | 0 | 0 |
| 5 (male) | 1 | 0.003 | 0 | 0 |
| 6 (female) | 0 | 0 | 0 | 0 |
| 7 (female) | 1 | 0.011 | 0 | 0 |
| 8 (male) | 0 | 0 | 0 | 0 |
| Mean | 0.3 | 0.002 | 0 | 0 |

EXAMPLE 2

Induction of tolerance to E-selectin. An analysis was performed to determine whether tolerance to E-selectin was induced by the intranasal administration protocol of E-selectin described above, which resulted in decreased stroke-related tissue damage. For this analysis, either E-selectin or control PBS preparations were administered to rats as described in Example 1 for the non-booster groups. Delayed-type hypersensitivity (DTH) was analyzed by injecting 5 µg of E-selectin in 50 µl of PBS and 50 µl of complete Freund's adjuvant into hindpads (s.q.) 14 days after intranasal administration. Fourteen days later, the rats were rechallenged by injecting 5 µg E-selectin in 50 µl PBS into the ear and ear thickness was measured with microcalipers (Mitsutoyo) 48 hours later.

Figure 7:
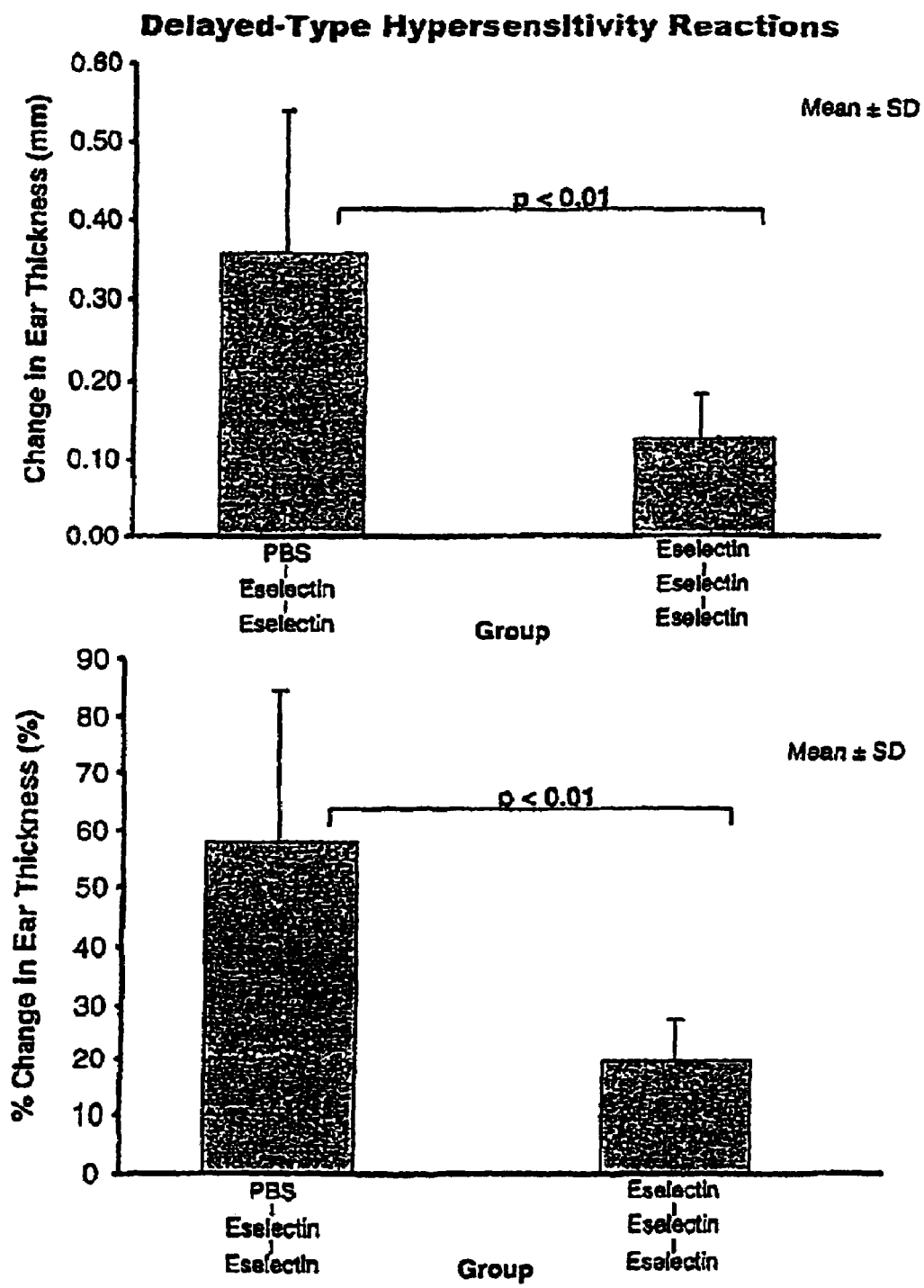
FIG. 7 is a series of bar graphs showing the effect of the tolerizing E-selectin regimen of the current invention on delayed-type hypersensitivity. For this experiment rats received an intranasal administration of E-selectin, then were immunized with E-selectin in the footpad prior to a booster immunization in the ear. The graphs illustrate the change in ear thickness of the ear that received the booster immunization of E-selectin compared to the ear that did not receive a booster administration. Panel A shows the increase in millimeters in the ear with the booster, and panel B present the increase in the ear receiving the booster in terms of percent change in ear thickness. Graphs on the left side of each panel show data for rats receiving control PBS administrations. Graphs on the right side of each panel show data for receiving an E-selectin tolerizing regimen according to the current invention.

Results of the delayed-type hypersensitivity assay demonstrated that intranasal instillation of human E-selectin induced tolerance. Administration of E-selectin intranasally prior to footpad injection and elicitation ear injection resulted in a significant suppression of ear swelling compared to control groups (FIG. 7), as measured with Mitsutoyo microcalipers. This data demonstrates that the E-selectin administration protocol used induced tolerance to E-selectin.

What is claimed is:

1. A method for reducing stroke-related tissue damage in a patient, said method comprising a series of intranasal administrations of human E-selectin.

2. The method of claim 1, wherein the series of intranasal administrations comprise a first series intranasal administrations of human E-selectin and a booster administration of human E-selectin comprising a second series of intranasal administration of human E-selectin.

3. The method of claim 2, wherein the first series of intranasal administrations and the second series of intranasal administrations each comprise five administrations of human E-selectin over a period of two weeks.

4. The method of claim 1, wherein each E-selectin administration is in an amount effective to induce E-selectin tolerance in the patient.

5. The method of claim 1, wherein the human E-selectin is soluble human E-selectin.

6. The method of claim 1, wherein the human E-selectin comprises human E-selectin lectin, EGF, CR1, and CR2 domains.

* * * * *